United States Patent [19]
Miller et al.

[11] Patent Number: 5,763,726
[45] Date of Patent: Jun. 9, 1998

[54] C₄/C₅ OLEFIN SKELETAL ISOMERIZATION PROCESS

[75] Inventors: Stephen J. Miller, San Francisco; John H. Shinn, Oakland, both of Calif.

[73] Assignee: Chevron U.S.A. Inc., San Francisco, Calif.

[21] Appl. No.: 872,295

[22] Filed: Jun. 10, 1997

Related U.S. Application Data

[60] Provisional application No. 60/021,208, Jul. 3, 1996.
[51] Int. Cl.⁶ .................. C07C 5/22; C07C 5/27
[52] U.S. Cl. .............. 585/671; 585/500; 586/671; 586/500
[58] Field of Search ................. 585/671, 500

[56] References Cited

U.S. PATENT DOCUMENTS

| | | | |
|---|---|---|---|
| 4,435,311 | 3/1984 | Sikkenga | 502/22 |
| 4,440,871 | 4/1984 | Lok et al. | 502/214 |
| 4,686,093 | 8/1987 | Flanigen et al. | 423/306 |
| 4,689,138 | 8/1987 | Miller | 208/111 |
| 4,943,424 | 7/1990 | Miller | 423/328 |
| 5,082,988 | 1/1992 | Holtermann | 585/739 |
| 5,107,047 | 4/1992 | Del Rossi et al. | 585/666 |
| 5,107,050 | 4/1992 | Gaffney et al. | 585/671 |

FOREIGN PATENT DOCUMENTS

| | | |
|---|---|---|
| 2123631 | 11/1994 | Canada. |
| 0 523 838 A2 | 1/1993 | European Pat. Off.. |
| WO 91/18851 | 12/1991 | WIPO. |

*Primary Examiner*—Elizabeth D. Wood
*Attorney, Agent, or Firm*—Alan W. Klaassen

[57] ABSTRACT

A C₄ and/or C₅ normal olefin isomerization process using a catalyst which contains SM-3 produces high yields of C₄ and/or C₅ iso-olefins.

16 Claims, 2 Drawing Sheets

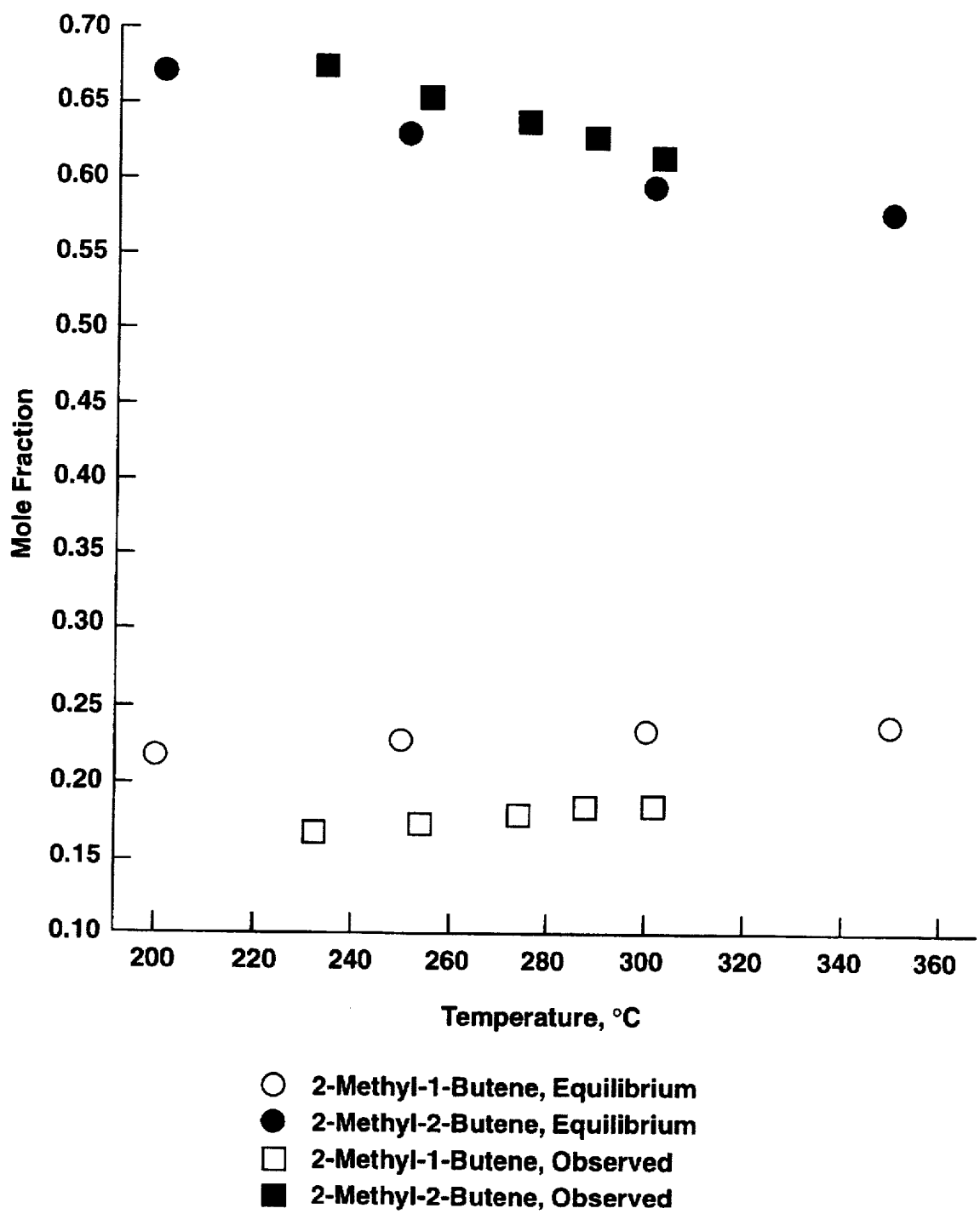

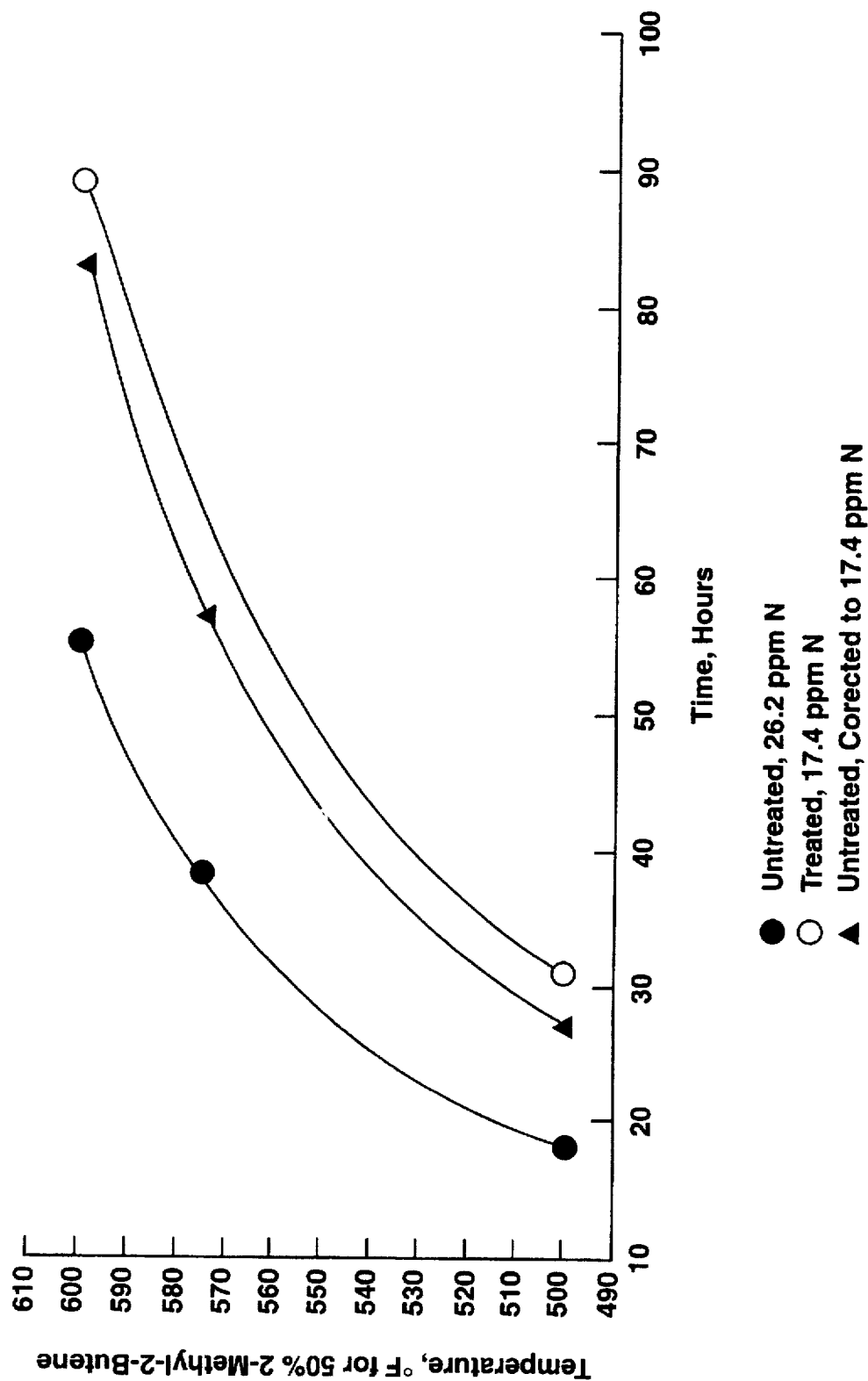

$C_4/C_5$ OLEFIN SKELETAL ISOMERIZATION PROCESS

This patent application claims priority from U.S. Provisional Patent Applicaton Serial No. 60/021,208 filed Jul. 3, 1996, the specification of which is incorporated herein by reference for all purposes

BACKGROUND OF THE INVENTION

1. Field of the Invention

This invention relates to an improved process for the conversion of hydrocarbons, and more specifically for the catalytic skeletal isomerization of olefinic hydrocarbons.

2. General Background

Olefinic hydrocarbons are useful as feedstocks in a variety of chemical, polymer and fuel applications. In many of these applications, the location of the double bond in the chain, the number of double bonds, and the location and number of branches, if any, are important. Since the olefinic hydrocarbons are available from a number of sources, including as product components of refinery processes, the location of double bonds and branching within the olefinic molecule from a particular source may not be optimum for its desired use.

$C_4$ and $C_5$ olefins are used as alkylating agents in the preparation of high octane gasoline. $C_4$ olefins and $C_5$ olefins are also reacted with alcohols to form oxygenates, which are included in motor gasoline by mandate of the Federal Clean Air Act and the California Air Resources Board. Two important oxygenates, methyl-tertiary-butyl-ether (MTBE) and tertiary-amyl-methyl-ether (TAME), are made by reacting $C_4$ and $C_5$ olefins respectively with methanol. However, only a portion of the $C_4$ and $C_5$ olefins react to form MTBE and TAME, i.e. those "etherable" olefin containing a branch adjacent to the double bond. The $C_4$ olefins (i.e., butenes, or butylenes) exist in four isomers. Three of these, 1-butene, cis-2-butene and trans-2-butene, are not branched, and are known collectively as normal or n-butenes. The fourth isomer, 2-methylpropene or isobutene, is branched. Conversion of a normal butene to isobutene is known as skeletal isomerization. Isobutene is an example of an etherable olefin. Likewise, $C_5$ olefins (i.e. pentenes) exist in five isomers. There are three normal or n-pentenes: 1-pentene, trans-2-pentene and cis-2-pentene, two branched etherable pentenes: 2-methyl-1-butene and 2-methyl-2-butene, and one branched non-etherable pentane: 3-methyl-1-butane.

As used herein, such etherable olefins containing a branch adjacent to the double bond are designated as "iso-olefins". A typical refinery stream containing $C_4$ and $C_5$ olefins typically contains a mixture of unbranched (i.e. normal) olefins and iso-olefins. It is therefore desirable to have a process for converting normal olefins present in the refinery stream to etherable iso-olefins.

U.S. Pat. No. 4,435,311 discloses processes for converting normal alkenes to isoalkenes using catalysts containing borosilicate zeolite. U.S. Pat. No. 5,510,560 discloses the skeletal isomerization of normal olefins of from 4 to 12 carbon atoms to provide a branched olefin product. The catalyst contains a zeolite in a binder, the zeolite having a pore size of at least about 4.5 angstroms and a pore structure characterized by intersecting 10-member ring and 8-member ring channels.

Silicoaluminophosphate molecular sieves are taught generally in U.S. Pat. No. 4,440,871. Non-zeolitic molecular sieves (NZMS) are taught, for example, in U.S. Pat. No. 4,861,743. Non-zeolitic molecular sieves are compositions having a three-dimensional microporous framework comprising $AlO_2$ and $PO_2$ units in tetrahedral coordination. Metalloaluminophophate molecular sieves that may be useful as isomerization catalysts are described in U.S. Pat. Nos. 4,500,651; 4,567,029; 4,554,143; and 4,686,093. The application of NZMS-containing catalysts to the isomerization of a $C_8$ aromatics stream is taught in U.S. Pat. No. 4,740,650. U.S. Pat. No. 4,689,138 teaches a process for isomerizing normal and slightly branched paraffins using a catalyst comprising a molecular sieve.

U.S. Pat. No. 5,132,484 teaches isomerizing butenes in a butene-containing feedstock with a catalyst containing at least one NZMS and having the substantial absence of a hydrogenation promoter, including a platinum group metal. The preferred product of the isomerization process of '484 is isobutene, and a preferred NZMS is SAPO-11. U.S. Pat. No. 5,146,035 teaches a skeletal isomerization process of a linear butene containing feedstock, where 0.1 to 5 mass % water is added to the reaction zone, and where the catalyst contains a NZMS selected from the group consisting of AlPOs, FAPOs, CoAPSOs, MnAPSOs, MgAPSOs and mixtures thereof. U.S. Pat. No. 5,191,146 teaches contacting a pentene-containing feedstock at isomerization conditions with a catalyst containing at least one NZMS to provide a product containing one or more of the isopentenes in greater concentration than in the feedstock.

SM-3, as disclosed in U.S. Pat. No. 4,943,424 and in U.S. Pat. No. 5,158,665, is a SAPO-11-type silicoaluminophosphate. An SM-3 catalyst containing a hydrogenation promoter is taught as being useful for selectively producing middle distillate hydrocarbons by hydrocracking a hydrocarbonaceous feed wherein at least 90% of the feed has a boiling point above about 600° F. SM-3 is also taught for dewaxing hydrocarbonaceous feeds, which normally are $C_{10}^+$ feedstocks boiling above about 350° F. A portion of the dewaxing reactions involve isomerization of n-paraffins to iso-paraffins to form liquid range materials which contribute to a low viscosity, low pour point product.

While skeletal isomerization of paraffins and alkyl aromatics is relatively straightforward, and acidic catalysts for these processes are readily available, catalytic processes for olefin skeletal isomerization are relatively non-selective, inefficient and short-lived. Olefins are relatively unstable, and easily polymerize, crack or transfer hydrogen during skeletal isomerization. In addition, it is well known that skeletal isomerization becomes more difficult as hydrocarbons get lighter. A selective, long-lived catalyst is therefore desired for the skeletal isomerization of $C_4$ and $C_5$ olefins. Furthermore, none of the publications described above teach or suggest the surprising catalytic performance of SM-3 in the skeletal isomerization of $C_4$ and $C_5$ normal olefins.

SUMMARY OF THE INVENTION

Accordingly, the present invention provides an isomerization process comprising contacting a normal $C_4$ and/or $C_5$ olefin containing feedstock with a catalyst comprising SM-3 at isomerization conditions sufficient to produce an isomerized product enriched in $C_4$ and/or $C_5$ iso-olefins relative to the feedstock.

Among other factors, the present invention is based on the discovery that SM-3 has surprising activity and selectivity in the skeletal isomerization of normal butenes and normal pentenes compared to the catalytic activity of conventional SAPO-11. Further to the surprise, SM-3 maintains the high activity and selectivity for skeletal olefin isomerization using refinery feedstocks having significant amounts of organic nitrogen present.

BRIEF DESCRIPTION OF THE DRAWINGS

FIG. 1 shows the amount of etherable $C_5$ olefin produced in the present process.

FIG. 2 shows the aging characteristics of the catalyst used in the present process.

DETAILED DESCRIPTION OF THE INVENTION

The feedstock containing the normal olefins to be isomerized in the present process includes product streams from petroleum-refining, synthetic-fuel, or petrochemical operations such as catalytic cracking, thermal cracking, steam pyrolysis, oligomerization, and Fischer Tropsch synthesis. These streams may require removal of polar contaminants such as sulfur, nitrogen or oxygen compounds by, e.g., extraction or adsorption, to maintain isomerization-catalyst stability. Removal of dienes and acetylenes, e.g., by selective hydrogenation or polymerization, also may be desirable.

An advantageous feedstock for iso-olefin production using the present invention is raffinate from an etherification process for producing oxygenates such as tertiary amyl methyl ether (TAME) or methyl tertiary butyl ether (MTBE). Such oxygenate preparation processes are well known in the art, and do not require detailed description here. Feeds to the etherification process may be pretreated by selective hydrogenation to remove diolefins. Additionally, an adsorption step using a zeolitic or clay adsorbent may be employed to remove nitrogenous species from the feed to the etherification process. Effluent from the etherification process is therefore enriched in unreacted linear $C_4$ and $C_5$ olefins, with a reduced concentration of nitrogenous and diolefinic species, both of which may be detrimental to the catalyst in the present process if present in sufficiently high concentrations. It is preferred that the concentration of organic nitrogen in the feed to the present process be less than about 40 ppm, preferably less than about 20 ppm, and that the concentration of diolefins in the feed to the present process, such as 1,4-pentadiene, be less than about 1 wt %. The use of at least a portion of the raffinate from the etherification unit as feed for the present process allows the present process to achieve a high level of conversion due to the low iso-olefin content of the feed, and allows for higher stability of the catalyst used in the present process because of removal of catalyst poisons in the hydrogenation and nitrogen adsorption units prior to etherification.

The feedstock in the present process contains at least one alkene or olefin having from 4 to 7 carbons. It is preferred that the feedstock to the present process contain at least one olefin selected from a $C_4$ olefin and a $C_5$ olefin. If the product from the present process is desired to include isobutene (otherwise known as isobutylene or 2-methylpropene), the feedstock to the present process should include one or more of the linear or normal butenes, i.e. 1-butene, cis-2-butene and trans-2-butene. If the product in the present process is desired to include one or more $C_5$ iso-olefins such as 2-methyl-1-butene and 2-methyl-2-butene, the feedstock to the present process should include one or more of the linear or normal pentenes, i.e. 1-pentene, cis-2-pentene and trans-2-pentene.

The normal $C_4$ and/or $C_5$ olefins are generally present in the feedstock in concentrations of greater than about 0.5 wt %. A typical olefin-containing stream from an FCC, which is useful as a feedstock in the present process, contains typically from about 1 to about 25 wt % normal olefins, and more generally from about 3 to about 20 wt % normal olefins. A typical effluent from an etherification unit which is suitable as a feedstock in the present process typically contains from about 1 to about 25 wt % normal olefins, and more generally from about 3 to about 20 wt % normal olefins. The feedstock may also contain $C_4$ and/or $C_5$ iso-olefins. However, the concentration of these iso-olefins will be low, typically less than about 3 wt % and preferably less than about 1 wt %.

In a specific embodiment of the invention, the present process comprises pretreating a $C_4$ and/or $C_5$ normal olefin-containing feedstock to produce a purified stream containing less than about 200 ppm water, less than about 50 ppm total oxygenates and less than about 40 ppm, preferably less than about 20 ppm organic nitrogen; and contacting the purified stream with a catalyst comprising greater than about 50% by weight of SM-3 to produce an isomerized product enriched in $C_4$ and/or $C_5$ iso-olefins relative to the feedstock. The $C_4$ and/or $C_4$ normal olefin-containing feedstock contains greater than about 0.5 wt % $C_4$ normal olefins and/or greater than about 0.5 wt % $C_5$ normal olefins. Streams containing $C_4$ normal olefins and no $C_5$ normal olefins, streams containing $C_5$ normal olefins and no $C_4$ normal olefins, and streams containing both $C_4$ and $C_5$ normal olefins may be treated by the present process.

When the feedstock contains $C_4$ normal olefins, the quantity of $C_4$ iso-olefins in the isomerized product is greater than the quantity of $C_4$ iso-olefins in the feedstock. Preferably, greater than about 1%, more preferably greater than about 5%, still more preferably greater than about 10%, and most preferably greater than about 20% of the $C_4$ normal olefins in the feedstock is converted to $C_4$ iso-olefins in the isomerized product.

When the feedstock contains $C_5$ normal olefins, the quantity of $C_5$ iso-olefins in the isomerized product is greater than the quantity of $C_5$ iso-olefins in the feedstock. Preferably, greater than about 1%, more preferably greater than about 5%, still more preferably greater than about 10%, and most preferably greater than about 20% of the $C_5$ normal olefins in the feedstock is converted to $C_5$ iso-olefins in the isomerized product.

SM-3, as disclosed in U.S. Pat. No. 4,943,424 and in U.S. Pat. No. 5,158,665, is a SAPO-11-type silicoaluminophosphate having a unique crystalline composition which provides improved catalytic performance in the present process. The entire disclosures of U.S. Pat. No. 4,943,424 and U.S. Pat. No. 5,158,665 are incorporated herein by reference.

The SM-3 silicoaluminophosphate, as-synthesized, has a crystalline structure whose X-ray powder diffraction pattern shows the following characteristic lines.

TABLE I

| 2θ | d | 100 × I/I$_o$ |
|---|---|---|
| 9.4–9.65 | 9.41–9.17 | m |
| 20.3–20.6 | 4.37–4.31 | m |
| 21.0–21.3 | 4.23–4.17 | vs |
| 22.1–22.35 | 4.02–3.99 | m |
| 22.5–22.9 (doublet) | 3.95–3.92 | m |
| 23.15–23.35 | 3.84–3.81 | m–s | m = 20–70
s = 70–90
vs = 90–100

After calcination, the SM-3 silicoaluminophosphate has a crystalline structure whose X-ray powder diffraction pattern shows the following characteristic lines as indicated in Table II below:

TABLE II

| 2θ | d | 100 × I/I₀ |
|---|---|---|
| 8.1 | 10.92 | m |
| 9.85 | 8.98 | m |
| 12.8 | 6.92 | m |
| 16.1 | 5.5 | m |
| 21.95 | 4.05 | vs |
| 22.3–22.5 | 3.99–3.95 | m |
| 23.5 | 3.786 | m |

The SM-3 silicoaluminophosphate molecular sieve as synthesized is characterized as comprising a three-dimensional microporous crystal framework structure of $SiO_2$, $AlO_2$, and $PO_2$ tetrahedral units which has a composition in terms of mole ratio of oxides on an anhydrous basis expressed by the formula:

$$mR:Al_2O_3:nP_2O_5:qSiO_2$$

wherein "R" represents at least one organic templating agent present in the intracrystalline pore system; "m" represents the moles of "R" present and has a value such that there are from 0.02 to 2 moles of R per mole of alumina; m has a value of from 0.1 to 4 and preferably 0.1 to 1; n has a value of from 0.94 to 1.1 and preferably 0.94 to 1; and q has a value of from 0.1 to 4 and preferably 0.1 to 1.

The SM-3 silicoaluminophosphate of this invention is further characterized in that the $P_2O_5$ to alumina mole ratio at the surface of the silicoaluminophosphate is about 0.85 or less and preferably in the range of 0.85 to 0.55, the $P_2O_5$ to alumina mole ratio of the bulk of the silicoaluminophosphate is 0.94 or greater, preferably in the range of 0.94 to 1.1, and most preferably in the range of 0.94 to 1, and the $SiO_2$ to alumina mole ratio at the surface of the silicoaluminophosphate is greater than the $SiO_2$ to alumina mole ratio within the bulk of the silicoaluminophosphate.

The SM-3 may be prepared as a catalyst having a wide variety of physical forms. Generally speaking, the SM-3 catalyst can be in the form of a powder, a granule, or a molded product, such as extrudate having a particle size sufficient to pass through a 2-mesh (Tyler) screen and be retained on a 40-mesh (Tyler) screen. In cases where the catalyst is molded, such as by extrusion with a binder, SM-3 can be extruded before drying, or, dried or partially dried and then extruded.

In the preparation of SM-3 as a catalyst, the SM-3 may also be composited with porous matrix materials and mixtures of matrix materials, such as silica, alumina, titania, magnesia, silica-alumina, silica-magnesia, silica-zirconia, silica-thoria, silica-beryllia, silica-titania, titania-zirconia, as well as ternary compositions such as silica-alumina-thoria, silica-alumina-titania, silica-alumina-magnesia and silica-magnesia-zirconia. The matrix can be in the form of a cogel. A preferred SM-3 catalyst contains greater than about 50% and preferably greater than about 75% SM-3 crystallites bound in an alumina matrix. The most preferred catalyst contains substantially no hydrogenation metal, e.g. Group VIII platinum-group metals such as platinum and palladium. By "substantially no hydrogenation metal" is meant that the most preferred SM-3 catalyst contains no Group VIII metal in sufficiently high concentrations to measurably affect the performance of the catalyst in the skeletal isomerization of normal $C_4$ and $C_5$ olefins as in the present invention. Catalysts containing a hydrogenation component at impurity levels such that the hydrogenation component does not deleteriously affect catalyst performance are acceptable.

The feedstock to the present process may contact the catalyst in the presence or in the absence of hydrogen. Typically, the feedstock contains less than 5 moles of hydrogen per mole of feedstock, and preferably in the range of 0.01 to 5, more preferably in the range of 0.1 to 3 moles of hydrogen per mole of feedstock. Hydrogen may be supplied totally from outside the isomerization process, or the outside hydrogen may be supplemented by hydrogen separated from product effluent from the isomerization process, and recycled to the feedstock. Inert diluents such as nitrogen, argon, methane, ethane and the like may be present. Although the principal isomerization reaction does not consume hydrogen, there may be net consumption of hydrogen in such side reactions as cracking and olefin saturation. In addition, hydrogen may suppress the formation of carbonaceous compounds on the catalyst and enhance catalyst stability.

The SM-3 containing catalyst in the reaction zone may be maintained during reaction as a fixed bed system, a moving bed system, a fluidized bed system or a batch reactor system. In general, the fixed bed system is the preferred system, based on ease of operation and reduced cost considerations, as well as for catalyst attrition considerations. Catalysts in olefin skeletal isomerization service which foul from catalyst poisons in the feed may require the use of a fluidized bed or moving bed system to facilitate catalyst removal during processing.

It is a feature of the present invention that the present isomerization process is preferably conducted in a fixed bed reaction system at a relatively low liquid hourly space velocity using a highly active, highly selective catalyst. The rate of passing the feedstock over the catalyst may be maintained at a sufficiently low rate that thermodynamic equilibrium is established between the normal olefins and iso-olefins. Alternatively, thermodynamic equilibrium may not be achieved in a single pass of reactants over the catalyst. To achieve high conversion, it may be desired to recover the iso-olefin products from the isomerization reactor effluent and to recycle at least a portion of the unreacted normal olefins to the isomerization reaction zone, and thereby increase the conversion of normal olefins to desired iso-olefins. The feed rate in the present process is such that the preferred liquid hourly space velocity, based on catalyst volume and volumetric rate of feed, is less than 5 hr$^{-1}$, more preferably in the range of about 0.5 to about 4 hr$^{-1}$. The conversion zone may be in one reactor or in separate reactors with suitable means therebetween to ensure that the desired isomerization temperature is maintained at the entrance to each reactor. The reactants may contact the catalyst in the liquid phase, a mixed vapor-liquid phase, or a vapor phase. Preferably, the reactants contact the catalyst in the vapor phase. The contact may be effected in each reactor in either an upward, downward, or radial-flow manner. Isomerization conditions include reaction temperatures generally in the range of from about 50° C. to 750° C. For the isomerization of butenes to increase the concentration of isobutene, temperatures in the range of 200° to 600° C. and especially 250° to 400° C. are preferred. Pentene isomerization is advantageously performed at temperatures in the range of about 200° to 600° C.; while 200° to 500° C. is preferred. Any convenient pressure can be used, with the lowest practical pressure being preferred in order to minimize side reactions such as polymerization. Reactor operating pressures usually will range from about atmospheric to 50 atmospheres preferably within the range of about 0.1 to about 10 atmospheres and most preferably about 1 to about 4 atmospheres.

The combination of the catalyst material and process conditions makes the process less susceptible to poisons obviating the need for sophisticated feed pretreatment (only drying to below 200 ppm water and preferably below 50 ppm total oxygenates is required). The catalyst and conditions further reduce the operating temperature of the process allowing for better conversion, better selectivity, and longer cycle time of the catalyst. The single fixed bed of catalyst is operated in semi-regenerative mode, i.e. the bed is operated on-stream for several months then taken off stream for a short period of time during which the catalyst is regenerated in-situ. This type of operation minimizes catalyst handling and requires only a single charge of catalyst be available. It further reduces the flow of regenerator off-gases and waste liquids minimizing the environmental liability of the process. Less feed pretreatment and a single simplified reaction system also reduce the capital requirements for the process compared with competitive processes. Operation of the single bed reaction system is considerably simpler and correspondingly less labor-intensive or costly than either the moving-bed or swing bed approaches in conventional olefin skeletal isomerization processes.

The present olefin isomerization process can be integrated with an etherification unit for the manufacture of ethers such as MTBE or TAME. The iso-olefin rich feedstock to the etherification unit is pretreated to reduce the nitrogen content of the feedstock. Suitable absorbents to remove the nitrogen compounds include heterogeneous acid catalysts such as acidic clays, molecular sieves and ion exchange resins. Such catalysts are described in U.S. Pat. No. 4,657,661, the entire disclosure of which is incorporated herein by reference for all purposes. The iso-olefin feedstock is then combined with an alcohol and reacted in the etherification unit to form the desired ether and a effluent raffinate stream which contains unreacted iso-olefins and normal olefins. It is a feature of the etherification reaction that diolefins are removed to low levels during the etherification reaction. After etherification the effluent raffinate stream is further treated to remove water and oxygenates, if necessary. The raffinate stream, characterized by a water content of less than about 200 ppm, a total oxygenate content of less than about 50 ppm, and an organic nitrogen content of less than about 40 ppm, is suitable as a feedstock in the present isomerization process. The feedstock to the isomerization process is then reacted, optionally in the presence of hydrogen, over SM-3 according to the present invention to form an effluent stream enriched in iso-olefins. As a further embodiment of the integrated process, at least a portion of the iso-olefin rich effluent stream may then be used as feedstock for the etherification process.

EXAMPLE 1

SM-3 sieve was prepared according to U.S. Pat. No. 5,208,005. Analyses are shown in Table III. The sieve was used to isomerize 1-pentene at 450° F., 1.0 WHSV, 0 psig, and 2 $H_2$/HC. At 15 hours onstream, the conversion of linear $C_5$ olefins was 86.5%, with 93.5% selectivity to iso-$C_5$ olefins. The product distribution is shown in Table IV.

FIG. 1 shows that the amount of etherable $C_5$ olefins produced over SM-3 was close to equilibrium.

Comparative Example

SAPO-11 was prepared according to Example 17 of U.S. Pat. No. 4,440,871. It was used to isomerize 1-pentene at the same conditions as in Example 1. Conversion to isomerized $C_5$ olefins was much lower than with the catalyst of the present invention.

Examples 2 and 3 illustrate the surprisingly high performance of the olefin isomerization catalyst in the presence of high concentrations of organic nitrogen in the feed.

EXAMPLE 2

SM-3 was tested for isomerizing the $C_5$ olefins in a refinery FCC $C_5$ cut (Table V). The nitrogen level in the feed was 26.2 ppm. The catalyst was tested at 50 psig, 1.0 WHSV, 2 $H_2$/HC, with temperature adjusted to maintain a 2-methyl-2-butene/total $C_5$ olefin product ratio of 0.50 (about 80% of the thermodynamic equilibrium ratio). After 56 hours, a catalyst temperature of 600° F. was required (FIG. 2).

EXAMPLE 3

The test of Example 2 was repeated, except that the feed was treated over an acidic montmorillonite clay (Harshaw-Filtrol F-24) to reduce the nitrogen level to 17.4 ppm. As seen in FIG. 2, a catalyst temperature of 600° F. was not required until the catalyst had been onstream for 90 hours.

TABLE III

| CATALYST PROPERTIES | | |
|---|---|---|
| Catalyst | SM-3 | SAPO-11 |
| $SiO_2/Al_2O_3$, bulk | 0.21 | 0.57 |
| $SiO_2/Al_2O_3$, surface | 0.74 | 1.34 |
| $P_2O_5/Al_2O_3$, bulk | 1.00 | 0.85 |
| $P_2O_5/Al_2O_3$, surface | 0.80 | 0.45 |

TABLE IV

Isomerization of 1-Pentene at
1-LHSV, 0 psig, 450° F., and 2 $H_2$/HC
at 15 hours Onstream

| Catalyst Product Distribution, Wt % | SM-3 | SAPO-11 |
|---|---|---|
| $C_4-$ | 0.0 | 0.0 |
| Isopentane | 0.72 | 0.70 |
| n-pentane | 1.80 | 2.01 |
| 1-pentene | 1.29 | 57.57 |
| 3-methyl-1-butene | 1.36 | 0.09 |
| trans-2-pentene | 8.71 | 23.34 |
| cis-2-pentene | 3.50 | 9.96 |
| 2-methyl-1-butene | 15.95 | 0.21 |
| 2-methyl-2-butene | 63.62 | 1.34 |
| $C_6+$ | 3.05 | 4.78 |
| | 100.00 | 100.00 |

TABLE V

| INSPECTIONS OF FCC $C_5$ CUT | |
|---|---|
| Carbon Number, Wt % | |
| $C_3$ | 0.2 |
| $C_4$ | 9.2 |
| $C_5$ | 73.0 |
| $C_6$ | 8.5 |
| $C_7+$ | 9.1 |
| Paraffins/Olefins/Naphthenes/Aromatic, wt % | |
| $C_4$ | 1.9/7.3/0/0 |
| $C_5$ | 37.8/34.9/0.3/0 |
| $C_6$ | 4.3/3.0/0.8/0.4 |
| $C_5$, Wt % | |
| isopentane | 33.6 |
| n-pentane | 4.2 |
| cyclopentane | 0.3 |
| cyclo-pentene | 1.0 |

TABLE V-continued

| INSPECTIONS OF FCC C$_5$ CUT | |
| --- | --- |
| 3-methyl-1-butene | 1.3 |
| 1-pentene | 3.8 |
| trans-2-pentene | 7.8 |
| cis-2-pentene | 4.1 |
| 2-methyl-1-butene | 7.1 |
| 2-methyl-2-butene | 9.2 |
| Diolefins | 0.6 |

What is claimed is:

1. An isomerization process comprising contacting a normal C$_4$ and/or C$_5$ olefin containing feedstock with a catalyst comprising SM-3 at isomerization conditions sufficient to produce an isomerized product enriched in C$_4$ and/or C$_5$ iso-olefins relative to the feedstock.

2. The process according to claim 1 wherein the feedstock contains from about 0.5 to 100 wt % normal C$_4$ olefins.

3. The process according to claim 1 wherein the feedstock contains from about 0.5 to 100 wt % normal C$_5$ olefins.

4. The process according to claim 1 wherein the olefin containing feedstock is raffinate from an etherification unit.

5. The process according to claim 1 wherein the olefin containing feedstock contains less than 40 ppm organic nitrogen.

6. The process according to claim 1 wherein the olefin containing feedstock is an olefin stream from an FCC.

7. The process according to claim 1 wherein the catalyst contains substantially no hydrogenation component.

8. The process according to claim 1 wherein the catalyst further comprises a porous matrix material comprising at least one of silica, alumina, titania, magnesia, silica-alumina and silica-magnesia.

9. The process according to claim 8 wherein the catalyst comprises greater than about 50 wt % SM-3.

10. The process according to claim 1 wherein SM-3 has the crystalline structure whose X-ray powder diffraction pattern shows the characteristic lines as indicated in Table II and wherein the P$_2$O$_5$ to alumina mole ratio at the surface of SM-3 is about 0.85 or less, the P$_2$O$_5$ to alumina mole ratio of the bulk of SM-3 is 0.94 or greater, and the SiO$_2$ to alumina mole ratio at the surface of SM-3 is greater than the SiO$_2$ to alumina mole ratio within the bulk of SM-3.

11. An integrated olefin isomerization process comprising:

a) pretreating a normal C$_4$ and/or C$_5$ olefin containing feedstock to produce a purified stream containing less than about 200 ppm water, less than about 50 ppm total oxygenates and less than about 40 ppm organic nitrogen;

b) contacting the purified stream with a catalyst comprising greater than about 50% by weight of SM-3 at isomerization conditions sufficient to produce an isomerized product enriched in C$_4$ and/or C$_5$ iso-olefins relative to the feedstock.

12. The process according to claim 11 wherein the purified stream is derived from an effluent stream from an etherification process.

13. The process according to claim 11 further comprising the step of combining the isomerized product with an alcohol and reacting under conditions sufficient to produce an ether.

14. The process according to claim 13 wherein the iso-olefin is isobutene, the alcohol is methanol and the ether is methyl tert-butyl ether.

15. The process according to claim 13 wherein the iso-olefin is isopentene, the alcohol is methanol and the ether is tertiary-amyl methyl ether.

16. An isomerization process comprising contacting a feedstock which contains normal C$_4$ and/or C$_5$ olefins with a catalyst containing SM-3 having the substantial absence of a platinum-group metal at a temperature in the range of 200° C. and 600° C. and a WHSV of less than 5 hr$^{-1}$ to produce an isomerized product enriched in C$_4$ and/or C$_5$ iso-olefins relative to the feedstock.

* * * * *